United States Patent [19]

O'Hara

[11] Patent Number: 5,144,955
[45] Date of Patent: Sep. 8, 1992

[54] DOPPLER VELOCITY MEASURING MEDICAL UNIT

[75] Inventor: Michael L. O'Hara, Miami Lakes, Fla.

[73] Assignee: Cordis Corporation, Miami Lakes, Fla.

[21] Appl. No.: 685,444

[22] Filed: Apr. 15, 1991

[51] Int. Cl.$^5$ .............................................. A61B 8/06
[52] U.S. Cl. ............................................. 128/662.06
[58] Field of Search ..................... 128/662.03–662.06

[56] References Cited

U.S. PATENT DOCUMENTS 5,002,058 3/1991 Martinelli ..................... 128/662.06
5,046,503 9/1991 Schneiderman ............... 128/662.06

OTHER PUBLICATIONS

Brochure, Millar MIKRO-TIP brand Doppler System.
Brochure, NuVEL Brand Doppler Diagnostic Catheter; NuMed of Hopkinton, N.Y.
Kern, Morton J., M.D., "Intracoronary Doppler Blood Flow Velocity Catheters".

*Primary Examiner*—Francis Jaworski
*Attorney, Agent, or Firm*—Gerstman & Ellis, Ltd.

[57] ABSTRACT

A medical probe such as a catheter comprises a flexible, elongated member having distal and proximal ends, with Doppler-type velocity measuring means carried within said probe adjacent said distal end, and electrical wires carried within the probe and communicating between the measuring means and the proximal probe end for connection to an electronic system for processing signals from the Doppler chip. By this invention, at least a portion of the probe, including the distal end and Doppler crystal has an ovoid cross-sectional shape. The portion has a maximum cross-sectional dimension and a minimum cross-sectional dimension substantially perpendicular thereto to provide lateral spaces for flow outside of the probe while the probe resides in a blood vessel.

20 Claims, 1 Drawing Sheet

DOPPLER VELOCITY MEASURING MEDICAL UNIT

BACKGROUND OF THE INVENTION

In the treatment of heart disease it is often desirable to measure the "global" blood flow rate, which is the measure of the entire flow of blood through the coronary artery where it joins with the aorta. In the prior art such blood flow, as well as selective coronary blood flows in branches of the coronary artery, may be measured typically with a Doppler-type blood flow measuring catheter which carries a Doppler measuring crystal in its tip, which crystal is electrically connected by a wire extending through the catheter from the distal tip to electronics located beyond the proximal end of the catheter.

Signals are emitted from the Doppler crystal at the distal end of the catheter, which signals bounce off of moving blood cells and are sensed. Through the Doppler effect, the velocity of the blood cells relative to the Doppler crystal can be determined, and from that the blood flow rate present in the vessel being measured is determined.

Medical probes which make use of such Doppler measuring means are at the present time commercially available. Such probes may be sheathed wire probes without a lumen, or catheters with a lumen to permit the flow of fluids to and from the site where the blood flow velocity is being measured.

Example, the Millar MIKRO-TIP brand Doppler system is commercially available, being typically a probe without a lumen having a Doppler chip velocity sensor adjacent its distal end. Also, the NuVEL brand Doppler diagnostic catheter is manufactured and sold by NuMed Inc. of Hopkinton, N.Y. Also, a Doppler flow measuring catheter is sold by the Cordis Corporation of Miami, Fla.

Other literature relating to Doppler blood flow velocity catheters exists as well. For example, the publication by Morton J. Kern, M.D. entitled Intracoronary Doppler Blood Flow Velocity Catheters is pertinent for a discussion of the background and use of such catheters.

When selective coronary flow is measured in a particular branch of the coronary artery system, a relatively narrow catheter or probe is used, which probe measures a much lower blood flow volume than in the case of the measurement of global flow at the junction of the coronary artery with the aorta. When one attempts to measure global flow in the enlarged junction of the coronary artery with a catheter which is narrow enough to measure selective coronary flow in branch arteries, for example using a NuVEL type guidewire device, disadvantages are found. This results at least in part from the fact that the flow through the trunk portion of the coronary artery is faster in the center than it is near the edges, in accordance with conventional fluid dynamics. When one attempts to measure blood flow velocity with a thin guidewire type Doppler device, the device may move laterally around inside the large coronary artery trunk, recording different flow rates when it is at a central portion in the artery than when it is adjacent the artery wall. Thus an inaccurate reading can result.

Accordingly, it is generally desirable to use a larger diameter catheter-type device for reading global coronary flow reserve. With the use of a soft, larger diameter catheter type structure, one can use the "pull back method" to pull the catheter up against the wall of the coronary trunk to stabilize it, to obtain a constant, reproducible global coronary artery flow reading.

However, it has been found that such catheters for reading global arterial flow, and which are of cylindrical cross section adjacent the distal tip, exhibit the disadvantage that the cylindrical cross section of the tip can tend to block flow to the coronary tree. In response to this, experimental efforts were made by others to place flow grooves in the periphery of the Doppler measuring catheter, without great success in remedying the flow obstruction problem. At the same time, a simple reduction of diameter of the catheter may not be feasible because of the need to incorporate near the tip a Doppler crystal and an injection lumen, and also for the reasons discussed above.

In accordance with this invention, a medical probe, typically a catheter, is provided in which a Doppler crystal can be accommodated, and also a lumen if desired, while at the same time adequate flow can be provided in the trunk of the coronary tree for adequate measurement of global blood flow through velocity measurement.

DESCRIPTION OF THE INVENTION

In this invention a medical probe is provided which comprises a flexible, elongated member having distal and proximal ends. Doppler-type velocity measuring means are carried within the probe adjacent the distal end. Electrical wire means are carried within the probe and communicate between the measuring means and the proximal probe end, for connection to an electronic system for processing signals from the measuring means.

At least a portion of the probe, including the distal end and the velocity measuring means, has an ovoid cross sectional shape, which is preferably substantially free of sharp edges. The probe portion has a maximum cross-sectional dimension and a minimum cross-sectional dimension which are substantially perpendicular to each other. The minimum cross-sectional dimension preferably is of essentially 0.4 to 0.9 times the distance of the maximum cross-sectional dimension.

Accordingly, the ovoid tip of the probe of this invention provides both adequate room in the tip for the Doppler crystal and also a lumen if desired, while at the same time providing adequate flow spaces between the ovoid tip and an artery into which it is inserted. The diameter of the artery will be, typically, approximately 0.03 to 0.09 inches more than the maximum cross-sectional diameter of the probe at the tip. Thus, substantial, adequate flow passages are provided between the minimum cross-sectional dimension areas of the tip and the artery wall.

Typically, the probe has a length which is in excess of 10 centimeters, generally on the order of 100 centimeters or so, with the ovoid portion thereof extending proximally from the distal end for a relatively minor portion of the overall length of the probe, the remainder of the probe being substantially of circular cross section. Typically, the ovoid portion tip may extend about 1 to 5 centimeters.

As previously stated, the probe of this invention is typically a catheter defining a lumen from end to end thereof, and which comprises a proximal Y-connection to define separate arms for, respectively, the lumen and the electrical wire means.

Typically, the velocity measuring means comprises a Doppler crystal, the probe defining a tip having a longitudinal axis, with the Doppler crystal being positioned in the probe tip laterally of the axis i.e., off center therefrom.

The probe of this invention, which is typically a catheter, is preferably proportioned to be of a transverse size to fit into the coronary artery of a patient at the junction with the aorta, while permitting blood flow through the artery for Doppler measuring of global coronary flow reserve. This avoids excessive lateral motion of the probe adjacent the junction of a type that would interfere with the Doppler measuring. Typically, the outer diameters of catheters of this invention are from about 0.066 in. to 0.136 in., and specifically 0.105 inch with this dimension being typically the same for the maximum cross-sectional dimension of the ovoid tip. The minimum cross-sectional tip dimension is typically about 0.033 in. to 0.116 in., specifically 0.065 to 0.075 inch, with the diameter of the flow lumen being about 0.046 inch in that particular embodiment. Similarly in that particular embodiment a second wire lumen present can have a diameter of about 0.012 in..

DESCRIPTION OF SPECIFIC EMBODIMENT

Figure 1:
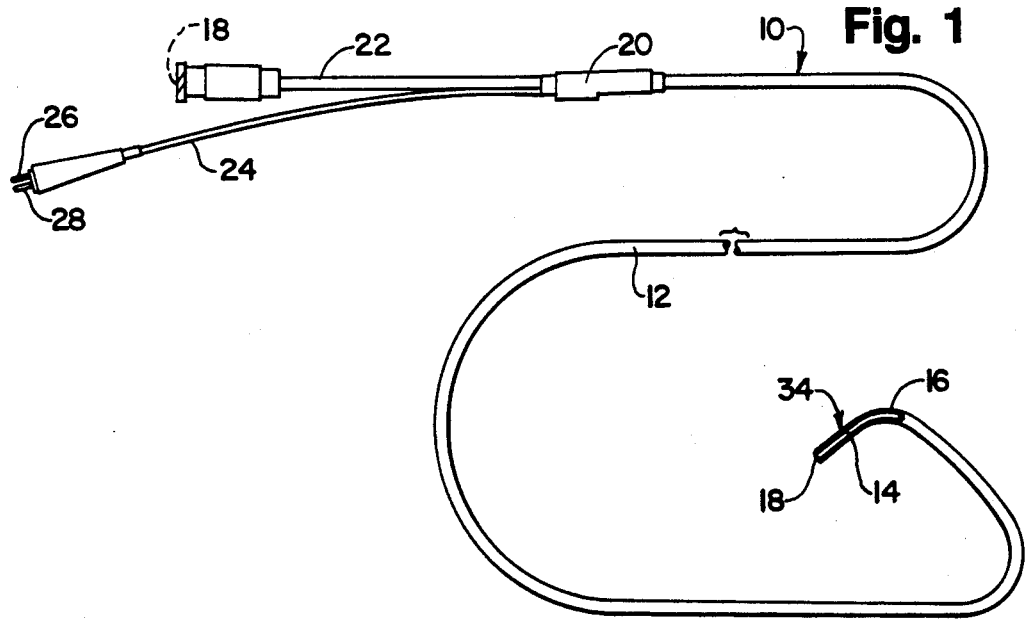
FIG. 1 is a plan view of a Doppler-type coronary flow measuring catheter in accordance with this invention.

Referring to the drawings, medical probe 10 is a catheter which comprises a flexible, elongated catheter shaft 12 having a catheter flow lumen 14 extending the length thereof, and a bend 16 adjacent the distal end 18 of the catheter to facilitate entrance of the distal tip 34 of the catheter into the coronary artery.

Near the proximal end of catheter 10, a Y-junction connector 20 is provided, dividing the catheter into two branches 22, 24. Lumen 18 extends through branch 22 to its proximal end, while wires 26, 28 project from the proximal end of branch 24 through wire lumen 27 and potted therein, extending the length of catheter 10 to a Doppler crystal 30 which is carried in the distal tip portion 34 of the catheter.

Doppler crystal 30 may be open to the exterior, being positioned in a cutaway portion 32 of the catheter wall, or, as shown, it may be secured with an encapsulating compound.

Figure 2:
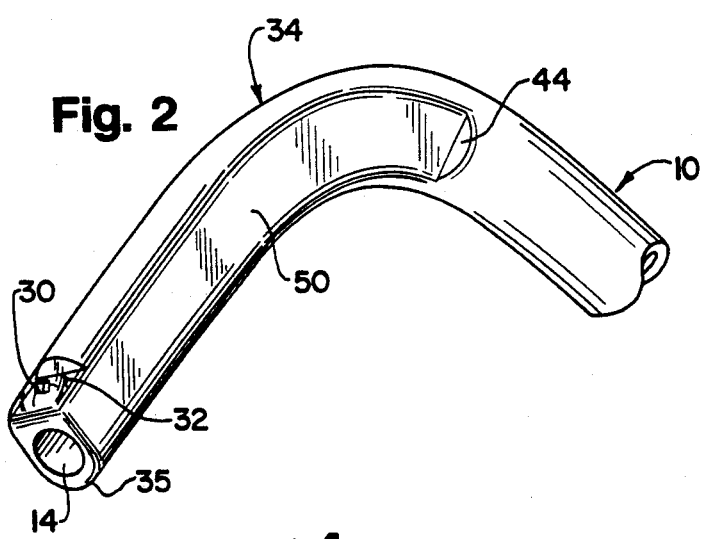
FIG. 2 is a fragmentary, perspective view of the distal tip of the catheter of claim 1.
Figure 3:
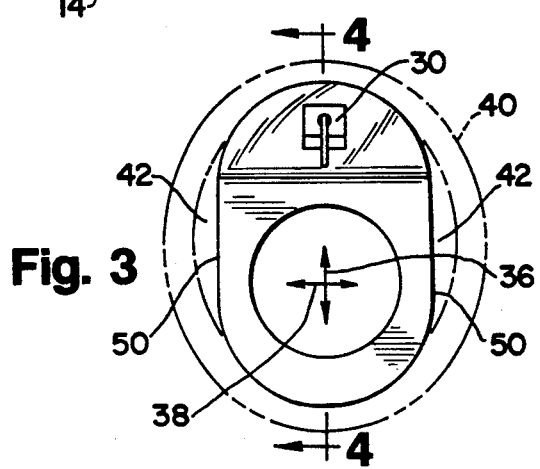
FIG. 3 is an enlarged, elevational view of the distal end of the catheter of FIG. 2.
Figure 4:
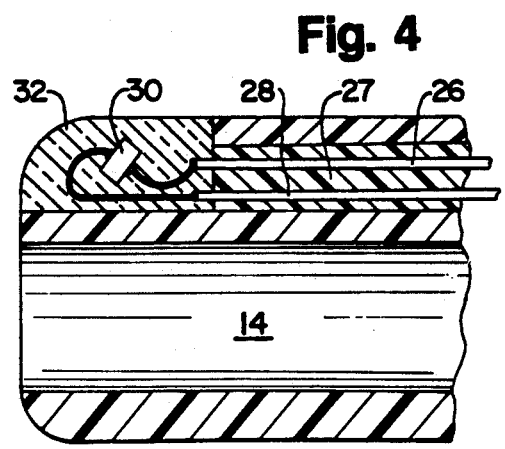
FIG. 4 is a sectional view taken along line 4—4 of FIG. 3.

In accordance with this invention, distal tip portion 34 of catheter 10 defines a ovoid cross sectional shape (FIG. 3) having a maximum cross-sectional dimension 36 and a minimum cross-sectional dimension 38, which is specifically shown to be about 0.6 to 0.7 (e.g. 0.675) times the distance of maximum cross-sectional dimension 36. It can be seen from FIGS. 1 and 2 that tip 34 having the ovoid cross-sectional dimension extends for only a minor portion of the longitudinal extent of catheter 10, being typically about 2 ½ centimeters in length.

Accordingly, because of the unique ovoid shape of catheter tip 34, the catheter tip can fit into a coronary artery 40, or other artery, with a fit along its long axis 36, but with a substantial space along its short axis between the artery wall and the wall of the catheter tip, as indicated by spaces 42. Thus, a good blood flow can be provided in the artery while the catheter resides there for Doppler measurement, while at the same time there is room in catheter tip 34 for both Doppler crystal 30 and flow lumen 14 to be placed in side-by-side relation.

The novel tip 34 of the catheter of this invention may be manufactufed by grinding the sides of an initially cylindrical catheter tip to remove plastic material from the catheter in the regions 50, to achieve substantially flat sides in those regions. Then, the catheter tip may be soaked in an appropriate solvent such as methylethylketone when the catheter is made of polyurethane, for example, and rubbed to smooth the front edges 35 and sharp corners that result from the grinding step at the junction of the flattened, ground surfaces 50 and the untouched, cylindrical portions of the catheter tip wall. Thus, a catheter tip is provided which may be substantially free of sharp corners or edges, but still is of generally ovoid shape to accomplish the advantages of this invention over the initial, cylindrical, unground catheter tip.

Typically, the ovoid cross section of catheter tip 50 is generally uniform throughout most of its extent, except perhaps at a short, transition area 44, where the ovoid cross section ends and the cylindrical cross section of the remaining catheter portion begins.

Alternatively, the grinding may form a tapered catheter tip so that a varying-dimension, ovoid cross section may be provided.

The above has been offered for illustrative purposes only, and is not intended to limit the scope of the invention of this application, which is defined in the claims below.

That which is claimed is:

1. A medical probe which comprises a flexible, elongated member having distal and proximal ends, Doppler-type velocity measuring means carried within said flexible, elongated member adjacent said distal end, and electrical wire means carried within said probe and communicating between said measuring means and the proximal probe end for connection to an electronic system, for processing signals from said measuring means, at least a portion of said flexible, elongated member, including said distal end and velocity measuring means, having an ovoid cross-sectional shape comprising a pair of opposed, substantially flattened surfaces, and opposed rounded surfaces connecting said opposed, flattened surfaces to define said ovoid shape, said portion having a maximum cross-sectional dimension and a minimum cross-sectional dimension substantially perpendicular to each other, said minimum cross-sectional dimension being of essentially 0.4 to 0.9 times the distance of the maximum cross-sectional dimension.

2. The medical probe of claim 1 which is a catheter, defining a lumen from end to end.

3. The medical probe of claim 1 which has a length in excess of 10 cm., and in which said ovoid portion thereof extends proximally from said distal end partway along said flexible, elongated member, the remainder of said probe being substantially of circular cross-section.

4. The medical probe of claim 3 in which said ovoid portion extends for about 1-5 cm. proximally from said distal end.

5. The medical probe of claim 3 which defines a lumen from end-to-end, and which comprises a proximal Y-connection to define separate arms for, respectively, said lumen and said electrical wire means.

6. The medical probe of claim 3 in which said ovoid portion is of generally uniform cross-section throughout most of its extent.

7. The medical probe of claim 1 in which said velocity measuring means comprises a Doppler crystal, said probe defining a distal tip having a longitudinal axis, said Doppler crystal being positioned in said distal tip laterally of said axis.

8. The medical probe of claim 1 which is of a transverse size to closely fit at its maximum cross-sectional dimension into the coronary artery of a patient at the junction with the aorta, while permitting blood flow through said artery for Doppler measuring of global coronary flow reserve, and avoiding excessive lateral motion of said probe adjacent said junction to not interfere with said Doppler measuring.

9. The medical probe of claim 1 in which said ovoid portion of the probe is substantially free of sharp edges.

10. The medical probe of claim 1 which is free of an inflatable balloon.

11. A catheter which comprises a flexible, elongated member having distal and proximal ends, Doppler-type velocity measuring means carried within said flexible elongated member adjacent the distal end, and electrical wire means carried within said catheter and communicating between said measuring means and the proximal probe end for connection to an electronic system for processing signals from the measuring means, at least a portion of the flexible, elongated member, including said distal end and velocity measuring means, having an ovoid cross-sectional shape comprising a pair of opposed, substantially flattened surfaces, and opposed, rounded surfaces connecting said opposed, flattened surfaces to define said ovoid shape, said portion having a maximum cross-sectional dimension and a minimum cross-sectional dimension substantially perpendicular thereto, said minimum cross-sectional dimension being of essentially 0.4 to 0.9 times the distance of the maximum cross-sectional dimension, said ovoid portion of the catheter extending proximally from said distal end for a portion of the length of the catheter, the remainder of said catheter being substantially of circular cross-section.

12. The catheter of claim 11 in which said velocity measuring means comprises a Doppler crystal, said catheter defining a distal tip having a longitudinal axis, said Doppler crystal being positioned in said catheter distal tip laterally of said axis.

13. The catheter of claim 12 in which said ovoid portion extends for about 1–5 centimeters proximally from said distal end, said catheter having a length in excess of 10 centimeters.

14. The catheter of claim 13 in which said ovoid portion of the probe is substantially free of sharp edges.

15. The catheter of claim 14 in which said ovoid portion is of generally uniform cross-section throughout most of its extent.

16. The catheter of claim 15 which is of a transverse size to fit into the coronary artery of a patient at the junction with the aorta, while permitting blood flow through said artery for Doppler measuring of global coronary flow reserve, and avoiding excessive lateral motion of said probe adjacent said junction to not interfere with said Doppler measuring. not interfere with said Doppler measuring.

17. The catheter of claim 16 which defines a lumen from end-to-end and which comprises a proximal Y-connection to define separate arms for, respectively, said lumen and said electrical wire means.

18. The catheter of claim 11 which is of a transverse size to fit into the coronary artery of a patient at the junction with the aorta, while permitting blood flow through said artery for Doppler measuring of global coronary flow reserve, and avoiding excessive lateral motion of said probe adjacent said junction to not interfere with said Doppler measuring.

19. The catheter of claim 11 in which said ovoid portion of the probe is substantially free of sharp edges.

20. The catheter of claim 11 in which said ovoid portion is of generally uniform cross-section throughout most of its extent.

* * * * *